(12) United States Patent
Hodge et al.

(10) Patent No.: US 7,238,654 B2
(45) Date of Patent: Jul. 3, 2007

(54) COMPATIBILIZING SURFACTANT USEFUL WITH SLURRIES OF COPPER PARTICLES

(75) Inventors: Robert L. Hodge, Sumter, SC (US); H. Wayne Richardson, Sumter, SC (US)

(73) Assignee: Phibro-Tech, Inc., Ridgefield Park, NJ (US)

( * ) Notice: Subject to any disclaimer, the term of this patent is extended or adjusted under 35 U.S.C. 154(b) by 179 days.

(21) Appl. No.: 11/053,437

(22) Filed: Feb. 9, 2005

(65) Prior Publication Data

US 2005/0256026 A1 Nov. 17, 2005

Related U.S. Application Data

(60) Provisional application No. 60/616,646, filed on Oct. 8, 2004, provisional application No. 60/571,535, filed on May 17, 2004.

(51) Int. Cl.
*C11D 1/835* (2006.01)
*C11D 3/12* (2006.01)

(52) U.S. Cl. ............ 510/199; 510/382; 510/383; 510/384; 510/397; 510/418; 510/421; 510/504; 106/15.05; 106/18.32; 106/18.36

(58) Field of Classification Search ............ 106/15.05, 106/18.32, 18.36; 510/199, 382, 383, 384, 510/397, 418, 421, 504
See application file for complete search history.

(56) References Cited

U.S. PATENT DOCUMENTS

| 4,879,083 | A |   | 11/1989 | Knudson et al. |         |
|-----------|---|---|---------|----------------|---------|
| 4,923,894 | A |   | 5/1990  | Kanda et al.   |         |
| 5,277,979 | A |   | 1/1994  | Kielbania, Jr. et al. | |
| 5,304,376 | A |   | 4/1994  | Friedrichs et al. |     |
| 5,536,305 | A |   | 7/1996  | Yu             |         |
| 5,552,378 | A |   | 9/1996  | Trinh et al.   |         |
| 5,688,492 | A | * | 11/1997 | Galley et al.  | 424/49  |
| 5,714,507 | A |   | 2/1998  | Valcke et al.  |         |
| 5,763,338 | A |   | 6/1998  | Sean           |         |
| 5,846,305 | A |   | 12/1998 | Payzant        |         |
| 5,874,025 | A |   | 2/1999  | Heuer et al.   |         |
| 5,874,476 | A |   | 2/1999  | Hsu et al.     |         |
| 5,942,217 | A | * | 8/1999  | Woo et al.     | 424/76.1|
| 5,972,266 | A |   | 10/1999 | Fookes et al.  |         |
| 6,521,288 | B2|   | 2/2003  | Laks et al.    |         |
| 6,753,035 | B2|   | 6/2004  | Laks et al.    |         |
| 2004/0011244 | A1 | * | 1/2004 | Cui et al.   | 106/2   |

FOREIGN PATENT DOCUMENTS

EP 0472973 A1 3/1992

OTHER PUBLICATIONS

Liu et al. "Use of Nanoparticles for Controlled Release of Biocides in Solid Wood," J. Appl. Polym. Sci. 79:458-465 (2001).
Liu et al. "Use of Nanoparticles for the Controlled Release of Biocides in Pressure-Treated Solid Wood," Presentation at American Chemical Society, Las Vegas, Oct. 1997.
Laks et al. "Polymer Nanoparticles as a Carrier System for Wood Preservatives," PowerPoint Presentation to Rohm & Haas under confidentiality agreement, Oct. 30, 1998 (even-numbered pages not available).
Liu et al. "Use of Nanoparticles for the Controlled Release of Biocides in Pressure-Treated Solid Wood" Polymer Preprints 38(2):624-625 (1997).
Liu et al. "Use of Polymeric Nanoparticles for Controlled Release of Biocides in Solid Wood" Abstract, GG3.4, Symposium GG Polymeric Materials - Drugs, Delivery and Devices Nov. 30 - Dec. 1 (1998), Proceedings published as vol. 550 of the Materials Research Society Symposium Proceedings Series.
Liu, "Use of Polymer Nanoparticles as Carriers for the Controlled Release of Biocides in Solid Wood," Dissertation for the Degree of Ph. D., Michigan Technological University (1999).
The Copper Champs? Unique Copper Hydroxide Formulations (Brochure), Nufarm Americas Inc. (2002).

* cited by examiner

*Primary Examiner*—Charles Boyer
(74) *Attorney, Agent, or Firm*—Morgan, Lewis & Bockius LLP

(57) ABSTRACT

The invention relates to a compatibilizing dispersant used in a slurry composition comprising a strongly cationic component and a strongly anionic component. More specifically, the invention relates to stable aqueous slurries comprising suspended particles of sparingly soluble salts, oxide, and/or hydroxides of copper and/or zinc. The slurry further comprises a quaternary amine compound present in a biocidally effective amount when the slurry is used in a manner that provides the sparingly soluble copper and/or zinc containing particles in a biocidally effective amount. The slurry further comprises an effective amount of a dispersant having a large non-ionic component.

34 Claims, No Drawings

COMPATIBILIZING SURFACTANT USEFUL WITH SLURRIES OF COPPER PARTICLES

CROSS-REFERENCE TO RELATED APPLICATIONS

This application claims priority to co-pending U.S. Patent Application Nos. 60/571,535 filed May 17, 2004, 60/616,646 filed Oct. 8, 2004, Ser. No. 10/868,967 filed Jun. 17, 2004, currently pending Ser. No. 10/961,155 filed Oct. 12, 2004, currently pending Ser. No. 10/961,206 filed Oct. 12, 2004, currently pending and Ser. No. 10/961,157 filed Oct. 12, 2004, currently pending the disclosures of which are incorporated herein by reference.

STATEMENT REGARDING FEDERALLY SPONSORED RESEARCH OR DEVELOPMENT not applicable

INCORPORATION-BY-REFERENCE OF MATERIAL SUBMITTED ON A COMPACT DISC not applicable

SEQUENCE LISTING not applicable

FIELD OF THE INVENTION

The present invention relates to a compatibilizing dispersant used in a slurry composition comprising a strongly cationic component and a strongly anionic component. More specifically, the invention relates to stable aqueous slurries comprising suspended particles of sparingly soluble salts, oxide, and/or hydroxides of copper and/or zinc. The slurry further comprises a quaternary amine compound present in a biocidally effective amount when the slurry is used in a manner that provides the sparingly soluble copper and/or zinc containing particles in a biocidally effective amount. The slurry further comprises an effective amount of a dispersant having a large non-ionic component.

BACKGROUND

Copper ions in aqueous media are toxic to fungi and bacteria because of their ability to destroy proteins in plant tissues. Copper compounds such as basic copper sulfate, copper oxychloride, and cuprous oxide are effective in preventing plant diseases such as late blight of potatoes and tomatoes, leaf blight of celery, and downy mildew of cucumbers and melons. Copper is also a primary component in wood preservation formulations. In the absence of complexing ligands, e.g., amines, nitriles, ammonia, or the like, the solubility of copper in water is extremely low. Therefore, to apply a sufficient amount of copper to a plant, seed, or substrate (such as wood, plastic, and the like), it is advantageous to apply the copper component as micron-sized to sub-micron-sized particles of a sparingly soluble copper salt.

As used here, for convenience and unless otherwise specified, the term "sparingly soluble copper salt" also specifically includes copper hydroxide, though a hydroxide would not normally be classified as a salt. Similarly, while the invention is discussed in terms of a sparingly soluble copper salt, the invention is equally useful for slurries comprising a sparingly soluble zinc salt, and also for slurries comprising copper(I) oxide, zinc oxide, or both. Particulate copper fungicide can be applied more homogeneously and effectively if it can be dispersed in a broad range of water qualities and suspended in the aqueous media for a prolonged period of time. Traditional copper fungicide formulations require large quantities of anionic dispersants or surfactants for dispersion and suspension in a broad range of water qualities. The behavior of particles of copper salts and copper hydroxide in an aqueous slurry is such that a strongly anionic dispersant is required to disperse and stabilize a slurry. Examples of the anionic surfactants or dispersant systems are sodium poly(meth)acrylate, sodium lignosulphonate, naphthalene sulphonate, etc. The term poly(meth)acrylate encompasses polymers comprising a major quantity (e.g., at least 30% by weight, typically at least 50% by weight) of acrylate monomers, e.g., polyacrylates, polymers comprising a major quantity of methacrylate monomers, e.g., polymethacrylates, and polymers comprising a major quantity of combined acrylate-containing and methacrylate-containing monomers.

Another useful class of biocides are cationic organic biocides such as quaternary amines. Synergy between combinations of copper salts and organic biocides are known. A problem exists, however, because a slurry of copper salt particles (including for purposes here, a slurry of copper hydroxide particles) requires a strongly anionic dispersant to achieve a stable slurry. Addition of a strongly cationic organic biocide will destabilize the slurry and cause agglomeration and settling of particles. Quaternary ammonium compounds react with the anionic systems causing coagulation and/or rapid sedimentation of the copper compound. Thus, a copper fungicide formulation comprising quaternary ammonium salts cannot be applied with homogeneity. Formulations to overcome this tendency often utilize extremely high concentrations of anionic dispersants, e.g., the greater of between 5 to 15 grams of surfactants per gram of quaternary ammonium compound, or between 0.8 to 2 grams dispersants per gram of copper-containing particles.

It is desirable to provide formulations comprising lesser amounts of surfactants while maintaining stability when a strongly cationic organic biocide is added to a slurry of copper-containing salts.

SUMMARY OF INVENTION

One object of the invention is to provide a stable water-based biocide comprising a biocidally effective amount of suspended particles of a sparingly soluble copper salt and a biocidally effective amount of a strongly cationic biocide, e.g., quaternary ammonium compounds such as didecyl dimethyl ammonium chloride, alkyl dimethyl benzyl ammonium chloride, didecyl dimethyl ammonium carbonate and didecyl dimethyl ammonium bicarbonate.

One aspect of the invention is a dispersant that will disperse and suspend the copper salts while not being adversely affected, for example coagulated or agglomerated or otherwise causing the suspension to settle, by the quaternary ammonium compound. The invention relates to an aqueous slurry comprising: 1) suspended solid particulates of a copper-containing slightly soluble salt (or hydroxide) and/or a zinc-containing slightly soluble salt (or hydroxide); 2) a biocidal quaternary ammonium compound; and 3) an effective amount of a dispersant having a significant non-ionic component comprising a hydrophobic fraction comprising between 4 and 20 carbon atoms and an ester fraction advantageously formed from between 2 and 100, for example between 4 and 20, of polymerized ethylene oxide monomers, propylene oxide monomers, or mixture thereof (most preferably ethylene oxide monomers) and optionally but advantageously further comprising a strongly anionic component, e.g., a phosphate, a sulfate, a sulfonate, or less preferably a carboxylate.

The invention also relates to a method for using an aqueous slurry composition as a biocide (usually as a fungicide), wherein said slurry composition comprises: 1) a plurality of micron-sized or advantageously sub-micron-sized copper-containing particles, zinc-containing particles, or both, 2) a quaternary ammonium compound present in an amount between about 1 part quaternary amine to between about 0.1 to 200, typically between about 0.5 to 50, parts of the copper-containing particles, zinc-containing particles, or both; and an effective amount of at least one dispersant having a significant non-ionic component comprising an ethylene oxide-based ester component and a hydrophobic component which may for example be a alkyl, aryl, alkenyl, or allkynyl group having between 6 and 20 carbon atoms, and advantageously further comprising a strongly anionic component such as a phosphate.

The particles generally have a $d_{50}$ (the diameter where 50% by weight of the particles present have a diameter equal to or less than the $d_{50}$) of between about 0.05 micron and about 5 microns, typically between about 0.1 microns and about 3 microns, preferably between 0.15 microns and 0.7 microns, and if used for wood preservation a $d_{50}$ between about 0.1 microns and 0.5 microns. The $d_{50}$ is also called the wherein the weight mean diameter of the particles. In all cases, advantageously the particle size distribution is narrow. For example, with respect to larger particles in the slurry, advantageously the $d_{95}$ (the diameter where 95% by weight of the particles present have a diameter equal to or less than the $d_{95}$) that is less than 4 times the $d_{50}$, preferably less than 3 times the $d_{50}$. Additionally, with respect to smaller particles in the slurry, advantageously the $d_{20}$ (the diameter where 20% by weight of the particles present have a diameter equal to or less than the $d_{20}$) that is less than ¼ times the $d_{50}$, preferably less than ⅓ times the $d_{50}$.

Exemplary dispersants include vegetable oil ethoxylates such as canola oil ethoxylates, soybean oil ethoxylates, fatty acid ethoxylates, or mixtures thereof, formed from the base oil or fatty acid and between 2 and 100, for example between 4 and 40, of polymerized ethylene oxide monomers, propylene oxide monomers, or mixture thereof (most preferably ethylene oxide monomers) and optionally but advantageously further comprising a strongly anionic component, e.g., a phosphate, a sulfate, a sulfonate, or less preferably a carboxylate.

It is central to the invention to have an effective amount of dispersants. In one embodiment of the invention, the slurry comprises at least 0.20, preferably at least 0.25, more preferably at least 0.28, for example between about 0.28 and about 0.5, grams of the dispersants of this invention per gram of copper salt (or hydroxide) particles. In another embodiment of the invention, the slurry comprises at least 0.0004 moles, preferably at least 0.00045 moles, more preferably at least 0.0005 moles, for example between about 0.0005 moles and about 0.0008 moles, of the dispersants of this invention per gram of copper salt (or hydroxide) particles. In another embodiment of the invention, the slurry comprises at least about 0.00045 mole, more preferably at least about 0.0005 mole, for example between about 0.0005 mole and about 0.0008 mole of the dispersants of this invention per 10 square meters of surface area of the copper salt (or hydroxide) particles. In another embodiment of the invention, the slurry comprises at least 0.00045 mole, more preferably at least 0.0005 mole, for example between about 0.0005 mole and about 0.0008 mole of the dispersants of this invention per 50 square meters of surface area of the copper salt (or hydroxide) particles. In another embodiment of the invention, the slurry comprises at least 0.00045 mole, more preferably at least 0.0005 mole, for example between about 0.0005 mole and about 0.0008 mole of the dispersants of this invention per 100 square meters of surface area of the copper salt (or hydroxide) particles.

DETAILED DESCRIPTION OF INVENTION

By "compatibility", and the term "stable slurry", herein is meant that a slurry comprising an effective amount of the copper salt particles and the quaternary amine compounds, exhibits greater than 80% suspensibility for at least about thirty minutes, utilizing an ASTM Method #: E1673-95 test. If the test is on a slurry concentrate, the suspensibility method that is used to measure compatibility is CIPAC MT 161.

By "water qualities" herein is meant the hardness of the water, where less than 200 ppm hardness (as $CaCO_3$) is considered to be high quality, between 200 ppm and 700 ppm is average quality, and greater than 700 ppm hardness is indicative of poor quality water.

By "prolonged period of time" herein is meant that the slurries are stable when tested using a modified ASTM Method #: E1673-95 test, where the modification is that the test duration is extended from 30 minutes to 3 hours. For use in foliar applications, a preferred slurry exhibits greater than 90% suspensibility for at least 30 minutes, and preferably at least an hour. For wood preservation uses, a preferred slurry exhibits greater than 97% suspensibility for at least 30 minutes, and preferably for at least 3 hours.

Another aspect of the present invention is stable aqueous sparingly-soluble copper salt slurries comprising quaternary ammonium compounds. In another embodiment, this invention discloses a method to formulate such formulations.

Another aspect of the present invention is the use of such formulations such as the stable aqueous sparingly-soluble copper salt slurries in 1) the foliar treatment of crops and plants, 2) the exterior treatment of seeds and/or soil, and 3) the preservation of wood by the injection of the stable aqueous slurry into the wood. The formulations of the present invention have the copper-containing particles dispersed and/or suspended in an aqueous media even in the presence of quaternary ammonium compounds.

As used herein, unless otherwise specified, copper salts have the copper as copper(II). Fungicidal copper oxide particles advantageously have most of the copper in the copper(I) form. This invention is applicable for slurries of copper(I)oxide and/or zinc oxide, both when admixed with one or more copper or zinc (sparingly soluble) salts or in a slurry with only oxides. Copper(I) oxide particles are readily suspended by the dispersants of the present invention.

Exemplary sparingly soluble copper salts useful in the present invention include copper sulfate, tribasic copper sulfate, copper chloride, basic copper chloride (copper oxychloride), copper bromide, copper iodide, copper carbonate, copper borate, basic copper borate, basic copper carbonate, copper hydroxide, basic copper phosphate, basic copper phospho-sulfate, basic copper nitrate, and mixtures thereof. Generally a basic copper salt incorporates one or more copper hydroxide groups in the crystal for each group of copper salt in the crystal. More preferred sparingly soluble copper salts include tribasic copper sulfate, copper oxychloride, copper borate, basic copper borate, basic copper carbonate, copper hydroxide, basic copper phosphate, basic copper phospho-sulfate, basic copper nitrate, and mixtures thereof. The most preferred sparingly soluble copper salts are copper hydroxide, basic copper carbonate, copper borate and/or basic copper borate, and mixtures thereof. The carbonate and the hydroxide cations help moderate pH in the micro-environment around particles, while borate has a separate biocidal effect. For example, U.S. Pat. No. 5,846,305 discloses a wood preservative composition comprising a copper compound, an amine solvent and a boron compound.

Preferred zinc salts useful in the present invention include: zinc sulfate, basic zinc sulfate, zinc chloride, basic zinc chloride, zinc bromide, zinc iodide, zinc carbonate, zinc borate, basic zinc borate, basic zinc carbonate, zinc hydroxide, basic zinc phosphate, basic zinc phospho-sulfate, basic zinc nitrate, and mixtures thereof. Generally a basic zinc salt incorporates one or more zinc hydroxide groups in the crystal for each group of zinc salt in the crystal. More preferred zinc salts include: basic zinc sulfate, basic zinc chloride, zinc borate, basic zinc borate, basic zinc carbonate, zinc hydroxide, basic zinc phosphate, basic zinc phosphosulfate, basic zinc nitrate, and mixtures thereof. The most preferred zinc salts are zinc hydroxide, basic zinc carbonate, zinc borate, and mixtures thereof. It is known to use zinc borate to protect cellulosic composites, including particleboard, hardboard and oriented strand board, from fungal decay, as described in U.S. Pat. Nos. 4,879,083; 5,763,338; and 5,972,266. Solid zinc borate is added to wood composites during manufacture, because its inherent low solubility reduces leaching of the preservative in high moisture environments. Examples of such zinc borate compound include zinc methaborate [$Zn(BO_2)_2$], basic zinc borate [$ZnB_4O_7 \times 2ZnO$] and zinc borate [$2ZnO \times 3B_2O_3 \times 3.5H_2O$]. Dev et al. (J Timb. Dev. Assoc., 1997) described a two-stage process for treating solid wood with zinc borate in which the wood is treated with solutions of borax and zinc chloride in two separate steps. However, the high cost of retreating and rehandling the wood makes the commercial use of such multi-stage processes unattractive, and, zinc borate is not particularly effective against mold fungi.

When used with either a copper salt or with a zinc salt, suspended particles of zinc oxide and/or copper(I) oxide are also a highly preferred adjuvant. In addition to the biocidal properties of zinc oxide and copper(I) oxide, if a formulation comprises zinc oxide and copper compounds, the corrosivity of the formulation is expected to be lower as compared to the corrosivity of the comparable formulation comprising copper compounds only. Such a property can be important, for example, in wood preservation uses.

Biocidal quaternary ammonium compounds have a general formula $NR_1R_2R_3R_4$—X, and include for example tetraalkyl ammonium salts, trialkyl aryl ammonium salts, trialkyl ammonium oxide salts, or mixtures thereof. Tertiary ammonium compounds (where one R is hydrogen) can be biocidal, but are usually less preferred than are the quaternary ammonium compounds. The alkyl R groups are in the range of $C_1$ to $C_{30}$, more typically $C_1$ to $C_{18}$. The alkenyl R groups are in the range of $C_1$ to $C_{30}$, more typically $C_1$ to $C_{18}$. The alkynyl R groups are in the range of $C_1$ to $C_{30}$, more typically $C_1$ to $C_{18}$. The aryl R groups are in the range of $C_5$ to $C_{30}$, more typically $C_5$ to $C_{12}$. The aralkyl R groups are in the range of $C_5$ to $C_{30}$, more typically $C_5$ to $C_{12}$. The aryl R groups are in the range of $C_5$ to $C_{30}$, more typically $C_5$ to $C_{12}$. The aryl R groups are in the range of $C_5$ to $C_{30}$, more typically $C_5$ to $C_{12}$. Preferably, at least one of the R groups is selected from the above and comprises 8 or more carbon atoms, more preferably 10 or more carbon atoms. One or more R groups may be selected from the group consisting of a $C_{1-4}$ hydroxyalkyl group, a $C_{1-4}$ alkyl group, a $C_{2-5}$ hydroxyalkenyl group, a $C_{2-5}$ hydroxyalkynyl group, a $C_{3-5}$ hydroxyaryl group. One R group may comprise an oxide link to another quaternary amine compound. X is any cation, and is typically selected from the group consisting of a chloride, bromide, carbonate, sulfate, acetate or phosphate ion. There are hundreds of biocidally effective quaternary ammonium salts, though most effective quaternary ammonium salts have at least one of the 4 substituents bonded with the nitrogen to comprise 8 or more carbon atoms.

Exemplary quaternary ammonium compounds include didecyl-dimethyl-amine salts, decyl-dimethyl-benzyl amine salts, N,N-dimethyl-1-dodecylamine-N-oxide, N,N-dimethyl-1-hexadecylamine-N-oxide, and so forth. Other examples of these quaternary ammonium compounds include didecyldimethylammonium chloride, didecyldimethylammonium ethosulfate, didecylmethylpropylammonium bromide, didecylmethylbutylammonium chloride, benzylhexadecyldimethylammonium chloride, didecylmethyl-4-chlorobenzylammonium chloride, didecylmethyl-3,4-dichlorobenzylammonium chloride, decyloctyldimethylammonium chloride, decyloctylbenzylmethylammonium chloride, decyldodecyldimethylammonium chloride, decyldodecylethylmethylammonium chloride, dodecylbenzyldimethylammonium chloride, tetradecylbenzyldimethylammonium chloride, diundecyldimethylammonium chloride, dinonylhydroxyethylmethylammonium chloride, didecylhydroxypropylmethylammonium chloride, and diundecyldihydroxyethylammonium chloride. Blends of compounds containing dioctyl, didodecyl and decyloctyl compounds or didecyl, didodecyl and decyldodecyl compounds may also be used. In addition, mixtures of $C_{12}$, $C_{14}$ and/or $C_{16}$ alkyldodecylbenzylammonium chlorides are useful in practicing the invention.

In a first embodiment of the invention, the dispersant is a non-ionic surfactant. Non-ionic surfactants are materials which carry no discrete charge when dissolved or suspended in aqueous media. The hydrophilicity of the surfactant is provided by hydrogen bonding with water molecules. Oxygen atoms and hydroxyl groups readily form strong hydrogen bonds. Such hydrogen bonding can provide a dispersion (suspensibility) or solubilization of the fungicide in neutral or alkaline media. Non-ionic materials useful for the present invention further include polyalkylene oxide block copolymers. Such block copolymers typically have at least one block segment comprising $-(AO)_x-$, wherein AO represents an oxyalkylene moiety and x is a number of about 1 to about 100. Preferably, AO represents either an ethylene oxide moiety or a propylene oxide moiety. The $-(AO)_x-$ block must be attached to a functional group differing in hydrophilicity (or hydrophobicity).

Exemplary surfactants/dispersants include ethoxylates of castor oil (ethyleneoxide degree of polymerization 30–60 ethoxy moieties); ethoxylates of tridecylalcohol(ethyleneoxide degree of polymerization 4–20); ethoxylates of a C10–C14 alcohol (ethyleneoxide degree of polymerization 4–20); ethoxylates of nonylphenol (ethyleneoxide degree of polymerization 6–50); ethoxylates of a fatty alcohol (ethyleneoxide degree of polymerization 3–20); ethoxylates of a sorbitol ester (ethyleneoxide degree of polymerization 10–40); ethoxylates of a sorbitan-tallate (ethyleneoxide degree of polymerization 10–40); ethoxylates of a tristyrphenol (ethyleneoxide degree of polymerization 3–20); ethoxylates of a isodecyl alcohol (ethyleneoxide degree of polymerization 3–10); ethoxylates of a isododecyl alcohol (ethyleneoxide degree of polymerization 3–10), or mixtures thereof.

A group of non-ionic surfactants useful in the context of the present invention includes a polycondensation product containing an alkylene glycol as a monomer. Exemplary compounds include a polyethylene glycol, a polypropylene glycol or a block polymer of ethylene glycol and propylene glycol. The degree of polymerization of these compounds is preferably in the range of about 5 to about 1,000, and more preferably in the range of from about 10 to about 500.

Non-ionic dispersants further include polyalkylene oxide block copolymers. Such block copolymers typically have at least one block segment comprising -(AO)$_x$-, wherein AO represents an oxyalkylene moiety and x is a number of about 1 to about 100. Preferably, AO represents either an ethylene oxide moiety or a propylene oxide moiety. The -(AO)$_x$- block must be attached to a functional group differing in hydrophilicity (or hydrophobicity). Such copolymers can be derived from higher alkylene oxides such as ethylene oxide, propylene oxide, butylene oxide, styrene oxide, etc. Such block copolymers typically contain a polyethylene oxide block which is relatively hydrophilic combined with another polyalkylene oxide block which is typically hydrophobic resulting in surfactant properties. Another non-ionic surfactant includes polyoxypropylene-polyoxyethylene block copolymer surfactants. Those surfactants comprising a center block of polyoxypropylene units (PO), and having a block of polyoxyethylene (EO) units to each side of the center PO block, are generally useful in the context of this invention, particularly where the average molecular weight ranges from about 900 to 14,000, and the percent of weight EO ranges from about 10 to 80. These types of surfactants are sold commercially as "Pluronics."

A second, and preferred, group of non-ionic surfactants useful in the context of the present invention includes etherified compound of the first group of compounds and an aliphatic alcohol, in such a manner, a dispersant having a polyethylene oxide block which is relatively hydrophilic combined with a long alkyl section, e.g., $C_6$ to $C_{30}$, which is typically hydrophobic can be obtained, resulting in surfactant properties. Exemplary compounds include polyethylene glycol oleyl ether (ethyleneoxide degree of polymerization 4 to 50), polyethylene glycol cetyl ether (ethyleneoxide degree of polymerization 4 to 50), polyethylene glycol stearyl ether (ethyleneoxide degree of polymerization 4 to 50), polyethylene glycol lauryl ether (ethyleneoxide degree of polymerization 4 to 50), polyethylene glycol tridecyl ether (ethyleneoxide degree of polymerization 4 to 50), polyethylene glycol nonylphenyl ether (ethyleneoxide degree of polymerization 4 to 50), polyethylene glycol octylphenyl ether (ethyleneoxide degree of polymerization 4 to 50), and the like. A preferred degree of polymerization for compounds in this class is in the range of from 4 to 20, for example between about 6 to about 12.

A subgroup of compounds is an etherified compound of the above-mentioned group of compounds and a higher fatty acid. Exemplary compounds include polyethylene glycol monolaurate (ethyleneoxide degree of polymerization 2 to 50), polyethylene glycol monostearate (ethyleneoxide degree of polymerization 2 to 50), polyethylene glycol monooleate (ethyleneoxide degree of polymerization 2 to 50), and the like.

Other non-ionic surfactants include polyoxypropylene-polyoxyethylene block copolymer surfactants. Those surfactants comprising a center block of polyoxypropylene units (PO), and having a block of polyoxyethylene (EO) units to each side of the center PO block, are generally useful in the context of this invention, particularly where the average molecular weight ranges from about 900 to 14,000, and the percent of weight EO ranges from about 10 to 80.

In addition, hydrophobically modified pluronic surfactants can be employed, wherein a modifying group (R) such as a methyl, ethyl, propyl, butyl, benzyl, etc. may be capping the terminal oxy alkaline group; e.g., R-(EO)$_n$—(PO)$_m$-(EO)$_n$—R.

Exemplary dispersants include linear alcohol alkoxylates, such as the linear alcohol ethoxylates or an ethyoxylated/propoxylated block. If desired, the alcohol alkoxylate is suitably end-capped with a lower alkyl group, and such a product is commercially available as POLY-TERGENT SLF-18 surfactant, available from BASF Corporation. Other useful anionics are polycarboxylated alcohol alkoxylates, preferably those selected from the group consisting of the acids or organic or inorganic salts of the following: polycarboxylated linear alcohol alkoxylates, polycarboxylated branched alcohol alkoxylates, polycarboxylated cyclic alcohol alkoxylates, and combinations thereof. Nonionic surfactants include, for example: alkylphenol ethoxylates, for example, ethoxylated nonyl phenol, alkylphenol ethoxylate or nonylphenol ethoxylate containing from about 1 to about 20 or more moles of ethylene oxide per mole of phenol.

A preferred group of compounds includes phosphate (or less preferably sulfate or sulfonate) ester of any of the above-mentioned groups of compounds. Exemplary compounds include polyethylene glycol oleyl ether phosphate (ethyleneoxide degree of polymerization 4 to 50), polyethylene glycol cetyl ether phosphate (ethyleneoxide degree of polymerization 4 to 50), polyethylene glycol stearyl ether phosphate (ethyleneoxide degree of polymerization 4 to 50), polyethylene glycol lauryl ether phosphate (ethyleneoxide degree of polymerization 4 to 50), polyethylene glycol tridecyl ether phosphate (ethyleneoxide degree of polymerization 4 to 50), polyethylene glycol nonylphenyl ether phosphate (ethyleneoxide degree of polymerization 4 to 50), polyethylene glycol octylphenyl ether phosphate (ethyleneoxide degree of polymerization 4 to 50), and the like.

As will be appreciated by those skilled in the art, suitable blends can be employed in the process of the present invention based on various combinations of the above-described surfactants.

The dispersant need be present in an effective amount. An effective amount of hexaethylene glycol monotridecyl ether phosphate is about 0.28 grams dispersant per gram of copper carbonate particles present, where the copper carbonate particles have a weight mean diameter of between about 0.1 and 0.2 microns where at least 80% by weight of the particles in the slurry have a diameter equal to or less than about 0.2 microns. In one embodiment of the invention, the slurry comprises at least 0.20, preferably at least 0.25, more preferably at least 0.28, for example between about 0.28 and about 0.5, grams of the dispersants of this invention per gram of copper salt (or hydroxide) particles. In another embodiment of the invention, the slurry comprises at least 0.0004 moles, preferably at least 0.00045 moles, more preferably at least 0.0005 moles, for example between about 0.0005 moles and about 0.0008 moles, of the dispersants of this invention per gram of copper salt (or hydroxide) particles.

The amount of dispersant may be related to the exterior surface area of the particles. Depending on particle morphology, one gram of copper carbonate particles of size 0.15 micron will have an exterior surface area of between about 10 and about 100 square meters. The BET surface area of one gram of copper hydroxide particles of size 0.15 micron (where the particles appear to be planar rather than spherical) will have an exterior surface area of about 90 square meters. In another embodiment of the invention, the slurry comprises at least 0.25 gram, more preferably at least 0.28 gram, for example between about 0.28 gram and about 0.5 gram of the dispersants of this invention per 10 square meters of surface area of the copper salt (or hydroxide) particles. In another embodiment of the invention, the slurry comprises at least 0.25 gram, more preferably at least 0.28 gram, for example between about 0.28 gram and about 0.5 gram of the dispersants of this invention per 50 square meters of surface area of the copper salt (or hydroxide) particles. In another embodiment of the invention, the slurry comprises at least 0.25 gram, more preferably at least 0.28 gram, for example between about 0.28 gram and about 0.5 gram of the dispersants of this invention per 100 square meters of surface area of the copper salt (or hydroxide) particles.

In another embodiment of the invention, the slurry comprises at least about 0.00045 mole, more preferably at least about 0.0005 mole, for example between about 0.0005 mole and about 0.0008 mole of the dispersants of this invention per 10 square meters of surface area of the copper salt (or hydroxide) particles. In another embodiment of the invention, the slurry comprises at least 0.00045 mole, more preferably at least 0.0005 mole, for example between about 0.0005 mole and about 0.0008 mole of the dispersants of this invention per 50 square meters of surface area of the copper salt (or hydroxide) particles. In another embodiment of the invention, the slurry comprises at least 0.00045 mole, more preferably at least 0.0005 mole, for example between about 0.0005 mole and about 0.0008 mole of the dispersants of this invention per 100 square meters of surface area of the copper salt (or hydroxide) particles.

A seed dressing formulation is applied in a manner known per se to the seeds employing the combination of the invention and a diluent in suitable seed dressing formulation form, e.g. as an aqueous suspension or in a dry powder form having good adherence to the seeds. Such seed dressing formulations are known in the art.

i.e., 342 parts per million hard water. An anionic/cationic mixture was considered compatible if it exhibited suspensibility greater than 80% for at least about thirty minutes. The suspensibility test method was equivalent to Collaborative International Pesticide Analytical Committee (CIPAC) Method MT 161. In both the comparative examples and in the examples, the suspensibility test was performed on aqueous slurries comprising: A) a synthetic water having 342 parts per million hardness; B) 0.33% by weight copper carbonate particles having a weight average particle size of about 0.15 micron with about 80% by weight of the particles having a diameter of 0.2 micron or less; C) about 0.57% by weight of the quaternary compound, and D) the surfactant system. Two quaternary amine formulations were tested, each containing a proprietary combination of didecyl-dimethyl-ammonium salts and alkyl dimethyl ammonium salts, where the salts were carbonates in a first test and chlorides in a second system. The results were identical, suggesting the suspensibility did not depend on the quaternary amine counter-ion. This 1:1.7 weight ratio of copper carbonate to quaternary amine salts contains a much higher loading of quaternary amine than would be used for example in wood preservation slurries, where the weight ration of copper carbonate to quaternary amine may range from 2:2 to about 10:1. As such, it is a worse case for wood preservative compositions, though such formulations with high quaternary amine loadings can be useful in foliar applications and in seed treatment applications, where the quaternary amine can in addition to its biocidal properties also provide stickiness.

Comparative Examples 1 and 2

The slurries of Comparative Example 1 includes a dispersant system that is available in the copper fungicide industry. Stable copper carbonate slurry concentrates commercially available from Phibro-Tech, Inc. comprise 36.4% copper carbonate, between 6 and 14% of a ~6000 molecular weight sodium polyacrylate, about 0.5 to about 1.6% of a naphthalene sulfonate formaldehyde condensate, about 0.4 to 0.8% sodium lauryl sulfonate, and a balance water. Comparative example 1 used this formulation, where the amounts of each surfactant were at the maximum of the ranges used by Phibro-Tech Inc. in their copper carbonate slurry concentrates. The compositions of the slurry concentrate and of the slurry tested in comparative example 1 are provided in Table 1.

TABLE 1

Concentrate and Slurry Compositions, Comparative Example 1 (weight %)

| Ingredient | Purpose | slurry concentrate, % | Slurry tested, % |
| --- | --- | --- | --- |
| Copper Carbonate | Active Ingredient | 36.36 | 0.33 |
| Sodium Polyacrylate | Dispersant | 14.1 | 0.128 |
| Napthalene Sulphonate | Dispersant | 1.6 | 0.015 |
| Sodium Lauryl Sulfate | Wetting Agent | 0.8 | 0.007 |
| Quaternary amine | Active Ingredient |  | 0.57 |
| Water (<50 ppm hardness) | Diluent/Carrier | Balance | Balance |

EXAMPLES

Compatibility in different formulations was tested by analyzing suspensibility in a synthetically prepared water, The suspensibility of comparative example 1, at 30 minutes, was 20.9% with the chloride salts of the quaternary amines and was 23.2% with the carbonate salts of the quaternary amines. The suspensibility of comparative example 1, at 3 hours, was 12.1% with the chloride salts of the quaternary amines and was 11.8% with the carbonate salts of the quaternary amines. This is much lower than the 80% minimum required for foliar applications, much less for the more stringent requirements of suspensibility for slurries used as an injected wood preservative.

The slurries of comparative example 2 also include a dispersant system that is normally used in the copper fungicide industry. Stable copper carbonate slurry concentrates commercially available from Phibro-Tech Inc. comprise 36.4% copper carbonate, between 6 and 10% of sodium lignosulphonate, about 0.6 to about 2% of a dodecylbenzene sulfonate, and a balance water. Comparative example 2 used this formulation, where the amounts of each surfactant were at the maximum range used by Phibro-Tech, Inc. in their copper carbonate slurry concentrates. The compositions of the slurry concentrate and of the slurry tested in comparative example 2 are provided in Table 2.

TABLE 2

Concentrate and Slurry Compositions, Comparative Example 2 (weight %)

| Ingredient | Purpose | slurry concentrate, % | Slurry tested, % |
|---|---|---|---|
| Copper Carbonate | Active Ingredient | 36.36 | 0.33 |
| Sodium lignosulphonate | Dispersant | 10 | 0.128 |
| Dodecylbenzene Sulphonate | Dispersant | 2 | 0.015 |
| Quaternary amine | Active Ingredient | | 0.57 |
| Water (<50 ppm hardness) | Diluent/Carrier | Balance | Balance |

The suspensibility of comparative example 2, at 30 minutes, was 17.2% with the chloride salts of the quaternary amines and was 18.5% with the carbonate salts of the quaternary amines. The suspensibility of comparative example 2, at 3 hours, was 14.4% with the chloride salts of the quaternary amines and was 12.7% with the carbonate salts of the quaternary amines. This is much lower than the 80% minimum required for foliar applications, much less for the more stringent requirements of suspensibility for slurries used as an injected wood preservative. Neither of these formulations were compatible with the high load quaternary ammonium formulations—neither of the slurry formulations exhibited anything close to the 80% suspensibility standard after 30 minutes.

Comparative Examples 3 and 4

The slurries of comparative examples 3 and 4 include a dispersant of the present invention, but the amount of the dispersant was not sufficient to adequately stabilize the slurry having the very high (0.57%) loading of quaternary amine. The slurries of Comparative Example 4 would provide a stable slurry, however, if the amount of quaternary amine was present in a concentration equal to or less than about 0.17%. The amount of dispersant needed can vary with particle size, particle morphology, the composition of the dispersant, the composition of the quaternary amine, and the amount of quaternary amine present in the slurry. It is within the skill of one skilled in the art, having benefit of this disclosure, to determine the effective amount of dispersant necessary to stabilize a slurry without undue experimentation.

A stable copper carbonate slurry concentrate commercially available from Phibro-Tech Inc. comprises 36.4% copper carbonate, 6% of a StepFac 8181™ (commercially available from Stepan Inc., and believed to be polyethylene glycol monotridecyl ether phosphate having about 6 moles ethylene oxide per mole of nonylphenol), and a balance water. Comparative example 3 used this formulation. The compositions of the slurry concentrate and of the slurry tested in comparative example 3 are provided in Table 3.

TABLE 3

Concentrate and Slurry Compositions, Comparative Example 3 (weight %)

| Ingredient | Purpose | slurry concentrate, % | Slurry tested, % |
|---|---|---|---|
| Copper Carbonate | Active Ingredient | 36.36 | 0.33 |
| Polyethylene glycol monotridecyl ether phosphate | Dispersant | 6 | 0.055 |
| Quaternary amine | Active Ingredient | | 0.57 |
| Water (<50 ppm hardness) | Diluent/Carrier | Balance | Balance |

The suspensibility of comparative example 3 at 30 minutes was 15.8% with the chloride salts of the quaternary amines and was 13.2% with the carbonate salts of the quaternary amines. The suspensibility of comparative example 3 at 3 hours was 12.5% with the chloride salts of the quaternary amines and was 11.1% with the carbonate salts of the quaternary amines. This is much lower than the 80% minimum required for foliar applications, much less for the more stringent requirements of suspensibility for slurries used as an injected wood preservative.

In comparative example 4, the amount of polyethylene glycol monotridecyl ether phosphate in the slurry concentrate was increased to 7%, increasing the amount of this dispersant in the slurry tested to 0.064%. The suspensibility of comparative example 4 at 30 minutes was 35.2% with the chloride salts of the quaternary amines and was 43.8% with the carbonate salts of the quaternary amines. The suspensibility of comparative example 4 at 3 hours was 19.7% with the chloride salts of the quaternary amines and was 21.9% with the carbonate salts of the quaternary amines. This is much lower than the 80% minimum required for foliar applications, much less for the more stringent requirements of suspensibility for slurries used as an injected wood preservative. Though there was a marked improvement over the suspensibility compared to that of comparative example 3 with only 0.055% polyethylene glycol monotridecyl ether phosphate, this formulation (having 0.064% polyethylene glycol monotridecyl ether phosphate) did not pass the 80% suspensibility criteria of the test used.

Example 5

The slurries of Example 5 included an effective amount of a dispersant system of the present invention to adequately stabilize the slurry having the very high (0.57%) loading of quaternary amine. The slurries of Example 5 were sufficiently stable that they could meet the more stringent criteria for suspensibility of a slurry intended for use as an injected wood preservative. The compositions of the slurry concentrate and of the slurry tested in example 5 are provided in Table 4.

TABLE 4

Concentrate and Slurry Compositions, Example 5 (weight %)

| Ingredient | Purpose | slurry concentrate, % | Slurry tested, % |
|---|---|---|---|
| Copper Carbonate | Active Ingredient | 36.36 | 0.33 |
| Polyethylene glycol monotridecyl ether phosphate | Dispersant | 10 | 0.091 |
| Quaternary amine | Active Ingredient | | 0.57 |
| Water (<50 ppm hardness) | Diluent/Carrier | Balance | Balance |

The suspensibility of example 5, at 30 minutes, was 97.8% with the chloride salts of the quaternary amines and was 98.2% with the carbonate salts of the quaternary amines. The suspensibility of example 5, at 3 hours, was 95.4% with the chloride salts of the quaternary amines and was 95% with the carbonate salts of the quaternary amines.

Formulation 5 was found to be compatible with the quaternary compounds such as didecyl dimethyl ammonium chloride, alkyl dimethyl benzyl ammonium chloride, didecyl dimethyl ammonium carbonate, and didecyl dimethyl ammonium bicarbonate.

The molecular weight of the quaternary amine salts was about 350. The molecular weight of the polyethylene glycol monotridecyl ether phosphate was about 550. Therefore, the molarity of the quaternary amine was about 10 times greater than the molarity of the dispersant. This suggests the primary action of the dispersant is on the copper carbonate particles, as opposed to the dispersant surrounding, complexing with, or isolating the quaternary amines in the liquid. The weight ratio of the dispersant to the copper carbonate in Example 5 was 1:3.6. This is a surprising result, since the weight ratio of 1:6 in comparative example 3 and of 1:5 in comparative example 4 did not provide the desired effectiveness at a 0.57% quaternary ammonium compound content.

Therefore, a minimum effective amount of hexa-ethylene glycol monotridecyl ether phosphate appears to be between about 0.19 grams and about 0.28 grams per gram of copper hydroxide particles present having a weight mean diameter of between about 0.1 and 0.2 microns.

These examples are meant to exemplify the invention, and should not be construed to limit the invention in any way. The invention is defined by the claims.

What is claimed is:

1. A stable aqueous biocidal slurry comprising:
   (a) a plurality of particles comprising a particle selected from the group consisting of a slightly soluble copper salt, a slightly soluble zinc salt, zinc oxide, or mixtures or combinations thereof, wherein the weight mean diameter of the particles is between about 0.05 micron and about 5 microns;
   (b) a biocidally effective amount of a biocidally active quaternary ammonium salt; and
   (c) an effective amount of at least one dispersant comprising a hydrophilic polyalkylene oxide portion having between 2 and 50 alkylene oxide units therein and a hydrophobic portion comprising eight or more carbon atoms, wherein the slurry when tested at its intended use concentration is stable if it exhibits suspensibility greater than 80% after thirty minutes when tested according to the Collaborative International Pesticide Analytical Committee Method MT 161.

2. The composition as recited in claim 1, wherein said particles comprise a slightly soluble copper salt.

3. The composition as recited in claim 2, wherein said copper salt is selected from the group consisting of tribasic copper sulfate, copper oxychloride, copper borate, basic copper borate, basic copper carbonate, copper hydroxide, basic copper phosphate, basic copper phospho-sulfate, basic copper nitrate, and mixtures thereof, and wherein the weight mean diameter of the particles is between about 0.15 microns and about 0.7 microns.

4. The composition as recited in claim 2, wherein said copper salt is selected from the group consisting of copper hydroxide, basic copper carbonate, copper borate, basic copper borate, and mixtures thereof, and wherein the weight mean diameter of the particles is between about 0.1 and about 3 microns.

5. The composition as recited in claim 1, wherein said zinc salt is selected from the group consisting of zinc sulfate, basic zinc sulfate, zinc chloride, basic zinc chloride, zinc bromide, zinc iodide, zinc carbonate, zinc borate, basic zinc borate, basic zinc carbonate, zinc hydroxide, basic zinc phosphate, basic zinc phospho-sulfate, basic zinc nitrate, and mixtures thereof.

6. The composition as recited in claim 1, wherein the weight mean diameter of the particles is between about 0.1 and about 0.5 microns.

7. The composition as recited in claim 1, wherein said quaternary ammonium compound has a general formula of N—R₁R₂R₃R₄—X, wherein $R_1$, $R_2$, $R_3$ and $R_4$ are selected from the group consisting of hydrogen, a $C_1$ to $C_{18}$ alkyl, a $C_1$ to $C_{18}$ alkoxy, a $C_1$ to $C_{18}$ alkenyl, a $C_1$ to $C_{18}$ alkynyl, a $C_5$ to $C_{12}$ aryl, a $C_5$ to $C_{12}$ aralkyl, or a $C_5$ to $C_{12}$ aroyl, wherein at least two R groups are not hydrogen and at least one R group comprises six or more carbon atoms, and wherein X is selected from the group consisting of hydroxide, chloride, fluoride, bromide, carbonate, bicarbonate, sulfate, nitrate, acetate, phosphate, or any mixture thereof.

8. The composition as recited in claim 7, wherein at least one of the R groups comprises more than 10 carbons.

9. The composition as recited in claim 2, wherein the majority of the quaternary ammonium salt present is a quaternary ammonium bicarbonate, a quaternary ammonium carbonate, or combination thereof.

10. The composition as recited in claim 1, wherein the slurry further comprises an anionic surfactant selected from the group consisting of sodium poly(meth)acrylate, napthalene sulphonate, sodium lauryl sulfate, sodium lignosulphonate, dodecylbenzene sulphonate, and mixtures thereof.

11. The composition as recited in claim 1, wherein said dispersant is selected from the group consisting of
  (i) a first group of non-ionic surfactants comprising a polycondensation product containing an alkylene glycol as a monomer;
  (ii) a second group of non-ionic surfactants comprising etherified compound of said first group of compounds and an aliphatic alcohol;
  (iii) a third group of compounds comprising an etherified compound of said first group of compounds and a higher fatty acid; and
  (vi) mixtures thereof.

12. The composition as recited in claim 11, wherein said alkylene glycol in said first group is selected from the group consisting of polyethylene glycol, polypropylene glycol and a block polymer of ethylene glycol and propylene glycol, and wherein the degree of polymerization of said polycondensation product is in the range of from about 5 to about 1,000.

13. The composition as recited in claim 11, wherein said etherified compound of said second group of non-ionic surfactants is selected from the group consisting of
  (i) polyethylene glycol oleyl ether with a ethyleneoxide degree of polymerization in the range of 4 to 50,
  (ii) polyethylene glycol cetyl ether with a ethyleneoxide degree of polymerization in the range of 4 to 50,
  (iii) polyethylene glycol stearyl ether with a ethyleneoxide degree of polymerization in the range of 4 to 30,
  (iv) polyethylene glycol lauryl ether with a ethyleneoxide degree of polymerization in the range of 4 to 30,
  (v) polyethylene glycol tridecyl ether with a ethyleneoxide degree of polymerization in the range of 4 to 30,
  (vi) polyethylene glycol nonylphenyl ether with a ethyleneoxide degree of polymerization in the range of 2 to 100,
  (vii) polyethylene glycol octylphenyl ether with a ethyleneoxide degree of polymerization in the range of 5 to 50, and
  (viii) mixtures thereof.

14. The composition as recited in claim 13, wherein said etherified compound of said second group of non-ionic surfactants is selected from the group consisting of
  (i) polyethylene glycol oleyl ether with a ethyleneoxide degree of polymerization in the range of 6 to 8,
  (ii) polyethylene glycol cetyl ether with a ethyleneoxide degree of polymerization in the range of 6 to 8,
  (iii) polyethylene glycol stearyl ether with a ethyleneoxide degree of polymerization in the range of 6 to 8,
  (iv) polyethylene glycol lauryl ether with a ethyleneoxide degree of polymerization in the range of 6 to 8,
  (v) polyethylene glycol tridecyl ether with a ethyleneoxide degree of polymerization in the range of 6 to 8,
  (vi) polyethylene glycol nonylphenyl ether with a ethyleneoxide degree of polymerization in the range of 6 to 8,
  (vii) polyethylene glycol octylphenyl ether with a ethyleneoxide degree of polymerization in the range of 6 to 8, and
  (viii) mixtures thereof.

15. The composition as recited in claim 11, wherein said etherified compound of said third group of non-ionic surfactants is selected from the group consisting of
  (i) polyethylene glycol monolaurate with ethyleneoxide degree of polymerization in the range of 2 to 30,
  (ii) polyethylene glycol monostearate with ethyleneoxide degree of polymerization in the range of 2 to 50,
  (iii) polyethylene glycol monooleate with ethyleneoxide degree of polymerization in the range of 2 to 50, and
  (iv) mixtures thereof.

16. The composition as recited in claim 11, wherein said dispersant comprises a phosphate ester of any of groups 1, 2, or 3.

17. The composition as recited in claim 11, wherein said dispersant comprises a phosphate ester of any of group 2.

18. The composition as recited in claim 16, wherein said dispersant is selected from the group consisting of
  (i) polyethylene glycol oleyl ether phosphate with ethyleneoxide degree of polymerization in the range of 4 to 50,
  (ii) polyethylene glycol cetyl ether phosphate with ethyleneoxide degree of polymerization in the range of 4 to 50,
  (iii) polyethylene glycol stearyl ether phosphate with ethyleneoxide degree of polymerization in the range of 4 to 30,
  (iv) polyethylene glycol lauryl ether phosphate with ethyleneoxide degree of polymerization in the range of 4 to 30,
  (v) polyethylene glycol tridecyl ether phosphate with ethyleneoxide degree of polymerization in the range of 4 to 30,
  (vi) polyethylene glycol nonylphenyl ether phosphate with ethyleneoxide degree of polymerization in the range of 2 to 100,
  (vii) polyethylene glycol octylphenyl ether phosphate with ethyleneoxide degree of polymerization in the range of 4 to 50, and
  (viii) mixtures thereof.

19. The composition as recited in claim 16, wherein said dispersant is selected from the group consisting of
  (i) polyethylene glycol oleyl ether phosphate with a ethyleneoxide degree of polymerization in the range of 6 to 8,
  (ii) polyethylene glycol cetyl ether phosphate with a ethyleneoxide degree of polymerization in the range of 6 to 8,
  (iii) polyethylene glycol stearyl ether phosphate with a ethyleneoxide degree of polymerization in the range of 6 to 8,
  (iv) polyethylene glycol lauryl ether phosphate with a ethyleneoxide degree of polymerization in the range of 6 to 8, (v) polyethylene glycol tridecyl ether phosphate with a ethyleneoxide degree of polymerization in the range of 6 to 8,
(vi) polyethylene glycol nonylphenyl ether phosphate with a ethyleneoxide degree of polymerization in the range of 6 to 8,
(vii) polyethylene glycol octylphenyl ether phosphate with a ethyleneoxide degree of polymerization in the range of 6 to 8, and
(viii) mixtures thereof.

20. The composition as recited in claim 1, wherein said dispersant comprises a polyalkylene oxide block copolymer comprising at least one hydrophilic block segment comprising -(AO)$_x$-, wherein AO represents a substituted or an unsubstituted oxyalkylene moiety, wherein x is a number of about 1 to about 100, and wherein said alkylene is in the range of C2–C4, and at least one segment that has a lower hydrophilicity than the hydrophilic block segment.

21. The composition as recited in claim 20, wherein said AO represents oxyalkylene moiety selected from the group consisting of ethylene oxide, propylene oxide, butylene oxide, and styrene oxide.

22. The composition as recited in claim 20, wherein said polyoxyalkylene block copolymer is a polyoxypropylene-polyoxyethylene block copolymer.

23. The composition as recited in claim 20, wherein said polyoxypropylene-polyoxyethylene block copolymer comprises a center block of polyoxypropylene units, and a block of polyoxyethylene units to each side of said center block of polyoxypropylene units, and wherein the average molecular weight is in the range of from about 900 to about 14,000, and wherein the weight percent of ethylene oxide ranges from about 10% to about 80%.

24. The composition as recited in claim 1, wherein said dispersant is a phosphate ester selected from the group consisting of
(i) polyethylene glycol oleyl ether phosphate with a ethyleneoxide degree of polymerization in the range of 6 to 8,
(ii) polyethylene glycol cetyl ether phosphate with a ethyleneoxide degree of polymerization in the range of 6 to 8,
(iii) polyethylene glycol stearyl ether phosphate with a ethyleneoxide degree of polymerization in the range of 6 to 8,
(iv) polyethylene glycol lauryl ether phosphate with a ethyleneoxide degree of polymerization in the range of 6 to 8,
(v) polyethylene glycol tridecyl ether phosphate with a ethyleneoxide degree of polymerization in the range of 6 to 8,
(vi) polyethylene glycol nonylphenyl ether phosphate with a ethyleneoxide degree of polymerization in the range of 6 to 8,
(vii) polyethylene glycol octylphenyl ether phosphate with a ethyleneoxide degree of polymerization in the range of 6 to 8, and
(viii) mixtures thereof; and
wherein the weight percent of said phosphate ester is in the range of from about 0.25 parts to about 0.42 parts by weight per part of particles of slightly soluble copper and/or zinc salts.

25. The composition as recited in claim 24 wherein said particles of slightly soluble copper and/or zinc salts comprise basic copper carbonate, and said dispersant comprises polyethylene glycol monotridecyl ether phosphate, wherein the weight ratio of said copper carbonate to said polyethylene glycol monotridecyl ether phosphate is between about 1:0.8 to about 1:0.1.

26. A stable aqueous biocidal slurry comprising:
(a) a plurality of particles comprising a particle selected from the group consisting of a slightly soluble copper salt, a slightly soluble zinc salt, or both, wherein the weight mean diameter of the particles is between about 0.05 micron and about 5 microns;
(b) a biocidally effective amount of a biocidally active quaternary ammonium salt; and
(c) an effective amount of at least one dispersant comprising a hydrophobic saturated or unsaturated alkyl or alkylaryl portion comprising between 10 and 24 carbon atoms, a hydrophilic portion comprising between 4 to 20 polymerized C2 to C8 alkoxy moieties, wherein at least half of the alkoxy moieties are ethoxy moieties, and a phosphate ester portion,
wherein the slurry when tested at its intended use concentration is stable if it exhibits suspensibility greater than 80% after thirty minutes when tested according to the Collaborative International Pesticide Analytical Committee Method MT 161, wherein said dispersant.

27. The composition as recited in claim 26 wherein the weight ratio of said particles to said dispersant is between about 1:0.8 to about 1:0.1.

28. The composition as recited in claim 26 wherein the slurry comprises between about 0.20 to about 0.5 grams of the dispersants per gram of said particles.

29. The composition as recited in claim 26 wherein the slurry comprises between about 0.0004 moles and about 0.0008 moles of the dispersants per gram of said particles.

30. The composition as recited in claim 26 wherein said particles comprise a copper salt selected from the group consisting of tribasic copper sulfate, copper oxychloride, copper borate, basic copper borate, basic copper carbonate, copper hydroxide, basic copper phosphate, basic copper phospho-sulfate, basic copper nitrate, and mixtures thereof, and the slurry comprises between about 0.00045 moles and about 0.0008 moles of the dispersants per 10 square meters of surface area of said copper salt and/or copper hydroxide particles.

31. The composition as recited in claim 26 wherein said particles comprise a copper salt selected from the group consisting of tribasic copper sulfate, copper oxychloride, copper borate, basic copper borate, basic copper carbonate, copper hydroxide, basic copper phosphate, basic copper phospho-sulfate, basic copper nitrate, and mixtures thereof, and the slurry comprises between about 0.00045 moles and about 0.0008 moles of the dispersants per 50 square meters of surface area of said particles.

32. The composition as recited in claim 26 wherein the slurry comprises between about 0.00045 moles and about 0.0008 moles of the dispersants per 100 square meters of surface area of said particles.

33. A method comprising preparing a stable aqueous slurry comprising:
1) mixing under turbulent conditions
(a) a plurality of particles comprising a particle selected from the group consisting of a slightly soluble copper salt and/or a plurality of particles comprising a slightly soluble zinc salt, wherein the weight mean diameter of the particles is between about 0.05 micron and about 5 microns;
(b) an effective amount of at least one non-ionic dispersant comprising a hydrophilic polyalkylene oxide portion having between 2 and 50 alkylene oxide units therein, wherein at least one half of the alkylene oxide units are ethylene oxide units, and a hydrophobic portion comprising between 10 and 24 carbon atoms;
  (c) water; and
  (d) optionally an anionic surfactant; and
(2) adding a biocidally effective amount of a quaternary ammonium compound of general formula N—$R_1R_2R_3R_4$—X, wherein at least one of $R_1$, $R_2$, $R_3$ and $R_4$ comprises more than 8 carbons, and wherein X is a cation.

34. The method as recited in claim 33,
(i) wherein said copper salt is selected from the group consisting of copper (II) sulfate, copper (II) chloride, copper (II) bromide, copper (II) iodide, copper (II) carbonate, copper (I) chloride, copper (I) bromide copper (I) iodide copper (II) oxychloride, tribasic copper sulfate, copper borate, basic copper borate, basic copper carbonate, copper hydroxide, basic copper phosphate, basic copper phospho-sulfate, basic copper nitrate, and mixtures thereof and; wherein said zinc salt is selected from the group consisting of zinc sulfate, basic zinc sulfate, zinc chloride, basic zinc chloride, zinc bromide, zinc iodide, zinc carbonate, zinc borate, basic zinc borate, basic zinc carbonate, zinc hydroxide, basic zinc phosphate, basic zinc phospho-sulfate, basic zinc nitrate, and mixtures thereof;

(ii) wherein said quaternary ammonium compound has a general formula of N—$R_1R_2R_3R_4$—X, wherein at least two of $R_1$, $R_2$, $R_3$ and $R_4$ are selected from the group consisting of alkyl in the range of $C_1$ to $C_{30}$, alkenyl groups in the range of $C_1$ to $C_{30}$, alkynyl in the range of $C_1$ to $C_{30}$, aryl in the range of $C_5$ to $C_{30}$, aralkyl in the range of $C_5$ to $C_{30}$, and aroyl in the range of $C_5$ to $C_{30}$, and wherein X is a cation; and (iii) wherein said at least one non-ionic dispersant is selected from the group consisting of
  (a) a first group of non-ionic surfactants comprising a polycondensation product containing an alkylene glycol as a monomer;
  (b) a second group of non-ionic surfactants comprising etherified compound of said first group of compounds and an aliphatic alcohol;
  (c) a third group of compounds comprising an etherified compound of said first group of compounds and a higher fatty acid;
  (d) a fourth group of compounds comprising phosphate ester of said second group of compounds;
  (e) polyalkylene oxide block copolymer; and
  (f) mixtures thereof.

* * * * *